(12) United States Patent
Cook

(10) Patent No.: US 6,554,808 B1
(45) Date of Patent: Apr. 29, 2003

(54) LUBRICATOR FOR A CATHETER GUIDE WIRE

(75) Inventor: Christopher Keith Cook, Bristol (GB)

(73) Assignee: United Bristol Healthcare NHS Trust, Bristol (GB)

( * ) Notice: Subject to any disclaimer, the term of this patent is extended or adjusted under 35 U.S.C. 154(b) by 150 days.

(21) Appl. No.: 09/655,888

(22) Filed: Sep. 6, 2000

(30) Foreign Application Priority Data

Sep. 7, 1999 (GB) .............................................. 9921149
Dec. 20, 1999 (GB) .............................................. 9930097

(51) Int. Cl.$^7$ ............................................ A61M 25/00
(52) U.S. Cl. ..................................................... 604/265
(58) Field of Search ................................. 604/265, 264, 604/280, 177, 172

(56) References Cited

U.S. PATENT DOCUMENTS

| | | | |
|---|---|---|---|
| 3,683,928 A | | 8/1972 | Kuntz .......................... 128/349 |
| 3,726,281 A | * | 4/1973 | Norton et al. ........... 128/349 R |
| 3,861,395 A | | 1/1975 | Taniguchi .................... 128/349 |
| 4,392,856 A | * | 7/1983 | Lichtenstein ................. 604/177 |
| 4,692,154 A | | 9/1987 | Singery et al. .............. 604/172 |
| 4,834,711 A | | 5/1989 | Greenfield et al. .......... 604/172 |
| 5,125,914 A | * | 6/1992 | Bassin .......................... 604/275 |
| 5,209,726 A | * | 5/1993 | Goosen ......................... 604/54 |
| 5,242,428 A | * | 9/1993 | Palestrant .................... 604/265 |
| 5,357,961 A | * | 10/1994 | Fields et al. | |
| 5,409,463 A | | 4/1995 | Thomas et al. .............. 604/167 |
| 5,776,111 A | * | 7/1998 | Tesio ............................ 604/264 |
| 5,810,884 A | * | 9/1998 | Kim ............................. 606/213 |
| 6,004,305 A | * | 12/1999 | Hursman et al. ............ 604/328 |

FOREIGN PATENT DOCUMENTS

WO WO 99/42155 8/1999

* cited by examiner

*Primary Examiner*—William E. Tapolcai
*Assistant Examiner*—Mohammad M. Ali
(74) *Attorney, Agent, or Firm*—Hunton & Williams

(57) ABSTRACT

A lubricator is provided which comprises a body closed at opposing ends so as to define a chamber filled with a lubricant. Apertures are provided through opposing end walls such that the guide wire can be passed through the lubricator thereby being wetted and lubricated by a motion of the lubricator with respect to the guide wire.

10 Claims, 2 Drawing Sheets

LUBRICATOR FOR A CATHETER GUIDE WIRE

The present invention relates to a lubricator for a catheter guide wire.

It is known, for example in angiographic techniques, to insert a catheter having an inflatable balloon at its distal end into a patient. In order to accurately position the catheter, a guide wire is first inserted into the patient, often at a remote site such as the femoral artery and the end of the guide wire is moved towards the target site. In order to achieve this, a guide wire is used which is sufficiently rigid to enable it to be pushed along the blood vessels of the patient and yet sufficiently flexible in order to make the necessary turns along its path within the body. The guide wire is often formed with a curved tip such that the tip may be used to control the path of the distal end of the guide wire. In order to do this, the wire is rotated by the operator. The wire is sufficiently rigid to transmit torque along the length of the wire so as to cause the orientation of the wire, and in particular the orientation of the curved section at the distal end, to rotate in order that the wire can be guided. Furthermore, such guide wires are typically provided with a hydrophilic coating which makes the wire very slippery when wet. This is useful within the context of the animal or human body in that it makes the wire self lubricating whilst it is within the body.

Once the distal end of the wire is in the target region, a catheter is then slid along the wire in order to carry out whichever medical procedure is involved.

It is vitally important that the friction between the guide wire and the catheter is as low as possible since friction causes the movement of the catheter over the guide wire to result in a force being exerted on the guide wire which in turn may give rise to motion of the guide wire within the patient. This is potentially disruptive to the medical procedure and could also give rise to unnecessary injury to the patient.

According to a first aspect of the present invention there is provided a lubricator for a guide wire, the lubricator comprising a chamber or channel having first and second openings formed therein, the openings being dimensioned such that a guide wire can extend through the chamber or channel and contact with the contents of the chamber, said openings being dimensioned so as to be larger than the guide wire such that the lubricator can be moved substantially freely along the guide wire.

It is thus possible to provide an apparatus through which a catheter guide wire, may pass in order that motion of the lubricator with respect to the catheter guide wire causes the surface of the guide wire to be lubricated. Thus the catheter guide wire may be inserted into the patient as described hereinbefore. The lubricator may then be drawn along the path of the guide wire which remains outside of the patient thereby causing the guide wire to become slippery. Thus when the catheter is moved over the guide wire, frictional contact between the catheter and the guide wire will be much reduced. This has the benefit of making it easier for the operator to move the catheter along the guide wire, and also means that less force will be transmitted from the catheter to the patient via the resilience of the guide wire. Furthermore, since there is a clearance between the lubricator and the guide wire, very little friction exists between the lubricator and the guide wire. This means the lubricator can be moved along the guide wire to lubricate it without giving rise to a significant risk of the guide wire moving within the body of the patient.

The lubricator may be made from plastics or some other low cost material such that the lubricator may be disposed of after a single use. This is advantageous since there is always a risk that blood products might contaminate the guide wire (which is only used once) and thereby contaminate the interior of the lubricator.

Preferably the first and second openings are dimensioned so as to substantially correspond to the dimensions of the exterior of the guide wire with a little bit of extra space so as to allow the guide wire to move relatively freely with respect to the lubricator but to prevent liquid from leaking rapidly therefrom. In order to further reduce leaks, the first and second openings may be formed as channels thereby ensuring that the local direction of the guide wire as it passes through the lubricator is aligned with the axes of the channels.

Advantageously a third opening may be provided in fluid flow communication with the chamber or channel such that the chamber may be filled, flooded or topped up if necessary. The third opening may be provided with a self healing membrane, for example of rubber or a similar material, such that a hypodermic needle may be used to inject saline or other lubricant into the chamber or channel and that the puncture hole is substantially sealed once the hypodermic needle is removed.

Preferably the lubricator is pre-filled with sterile saline or other lubricant at manufacture and the apertures thereof are sealed. Advantageously the openings may be sealed with frangible membranes arranged such that the introduction of the medical device, such as a guide wire into the lubricator causes the frangible membranes to be ruptured. It is thus possible to provide a device which is permanently ready for use and sterile.

Preferably one end of the device, namely that end intended to be closest to the patient, is provided with engagement means for engaging a stabilising device. The engagement means may be in the form of resiliently deformable tines, a snap fixing, a screw thread or some other suitable mechanical arrangement. A complimentary fixing is provided on the stabilising device.

The stabilising device is arranged, in use, to encircle the medical device, for example a guide wire, and is provided with engagement members which can be moved between a first position such that they firmly engage the guide wire to a second position such that the guide wire is no longer held by the engagement members and the catheter can be passed through the stabilising device and into the patient. This enables the operator to hold the stabilising device steady, and hence hold the guide wire steady, whilst the guide wire is being lubricated and the catheter is being passed along the guide wire and towards the patient.

The channel is preferably elongate. In one embodiment the channel may be "closed", that is in a form of a pipe with a continuous outer surface. Thus the channel may, for example, be a cylinder open at opposing ends to form the first and second openings.

Alternatively, the channel may be "open" such that the guide wire, or some other medical device can enter the channel from the side. This effectively allows the lubricator to be clipped on or around the guide wire. The channel may be profiled so as to inhibit the accidental lateral removal of the device from the channel. The channel may include a non-linear, for example curved or serpentine, side entry channel and/or may be provided with lips and/or seals, thereby serving to prevent accidental disengagement of the lubricator from the medical device.

As a further alternative the body of the lubricator may be split into opposing parts such that the lubricator can be assembled around the guide wire. The opposing parts may be hingedly connected to one another and/or may engage each other in a snap fit manner or may use some other locking arrangement to hold the body parts together.

Advantageously the at least one supply channel engages with a receptor for a syringe such that the syringe can act as a reservoir for a lubricant. Alternatively a sponge or similar lubricant bearing insert may be provided within the body so as to act as a reservoir. The sponge like insert may be removable and replaceable. If a sufficiently rigid sponge is used the sponge may form the body of the lubricator. In such circumstances it is desirable that the outer surface of the sponge be treated to make it impermeable.

The present invention will further be described, by way of example, with reference to the accompanying Figures, in which.

Figure 1:
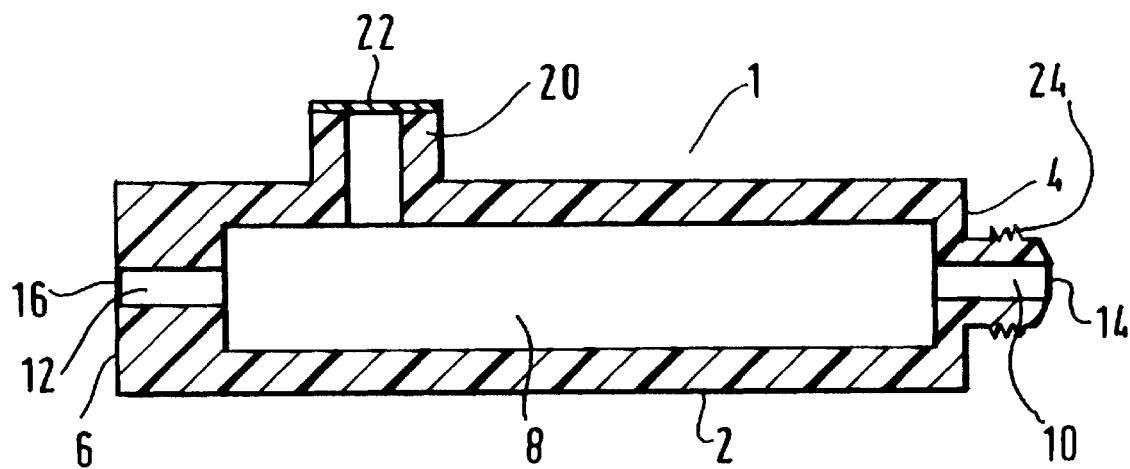
FIG. 1 is a cross section through a lubricator constituting an embodiment of the present invention.

A lubricator, generally indicated at 1, is shown in FIG. 1. The lubricator comprises a hollow element 2 which is closed by a first end wall 4 and a second end wall 6 so as to define a chamber 8 therein. A first opening 10 is provided in the first end wall 4. A second opening 12 is provided in the second end wall 6. The first and second openings 10 and 12 are substantially coaxially aligned with one another. As shown in FIG. 1, each opening is elongated to form a cylindrical conduit. Furthermore, each opening is dimensioned so as to be only slightly bigger than the external diameter of the catheter guide wire with which the lubricator is intended to be used. In use, the guide wire (not shown) extends through the second opening 12, through the chamber 8, and through the first opening 10 towards the patient. The chamber 8 is filled with a lubricating fluid, for example a sterile saline solution.

The lubricator may be pre-filled at manufacture with sterile saline and then the apertures closed by frangible membranes 14 and 16. These membranes which may, for example, be of a thin aluminised film, are punctured by the guide wire as it is passed through the lubricator. Additionally and/or alternatively, a third opening 20 may be provided in fluid flow communication with the chamber 8 such that fluid may be introduced into the chamber either before use of the lubricator, or during use of the lubricator. Advantageously, the third opening 20 is provided with a one way valve or a self sealing element. In the embodiment shown, a self healing elastomeric membrane 22 seals the third aperture. Thus sterile saline may be injected into the chamber 8 using a hypodermic needle piercing the membrane 22. Once the needle is removed, the membrane self seals thereby preventing loss of liquid through the third aperture.

The lubricator is provided with engagement means at or adjacent the end thereof intended to face towards the patient. In the embodiment illustrated, the engagement means is in the form of an externally screw threaded element 24.

Figure 2:
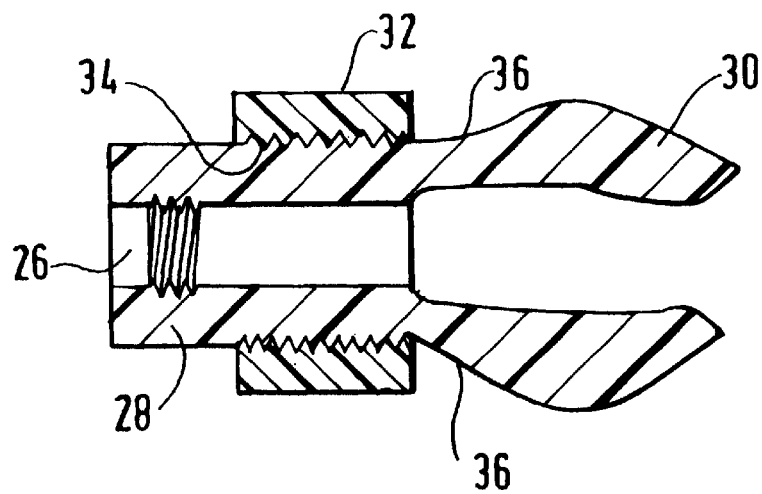
FIG. 2 is a cross section through a stabilising device which is adapted to be removeably attachable to the lubricator shown in FIG. 1.

The externally threaded element 24 co-operates with a reception region 26 of a stabilising device, generally indicated as 28 and illustrated in FIG. 2. The stabilising device encircles the guide wire as it passes therethrough. The stabilising device comprises a plurality of engagement elements 30, for example in the form of deformable fingers which can be caused to move from an unengaged position (as shown in FIG. 2) to an engaged position. In order to do this, an internally threaded collar 32 engages with a threaded portion 34 such that the collar can be made to translate axially along the stabilising device. As the collar 32 moves towards the fingers 30, it bears against the ramped profile 36 and pushes the surface inwardly towards the central axis of the device. As it does so, it causes the resilient fingers 30 to move towards the axis of the device, and thereby to engage with and hold a guide wire disposed between the fingers.

In use, the stabilising device is attached to the lubricator and the guide wire is passed through the combination and then into the patient. The stabiliser may be selectively done up and undone in order to grip the guide wire and allow it to be manipulated and turned, as appropriate, in order that the wire can be guided through the patient to reach a target site. Once the guide wire is correctly in position, the stabiliser is tightened again so as to hold the wire firmly and then the interconnection between the stabiliser and the lubricator is broken/undone thereby allowing the lubricator to be slid along the path of the guide wire, thereby wetting its external surface. During this process, the lubricator is removed completely from the guide wire. Whilst the surface of the guide wire is still wet and slippery, the catheter is slid along the guide wire until its distal end is adjacent the stabiliser. The stabiliser is then released, allowing the fingers 30 expand to the position shown in FIG. 2, and the catheter is then further slid along the guide wire passing through the stabiliser, and into the patient. The lubricator of the present invention may be used with other invasive medical instruments. Thus an enlarged version may be used to wet the external surfaces of endoscopes and gastroscopes. Such lubrication would aid the passage of the device within the body, and thereby reduce trauma and/or damage associated with use of such a device.

Figure 3:
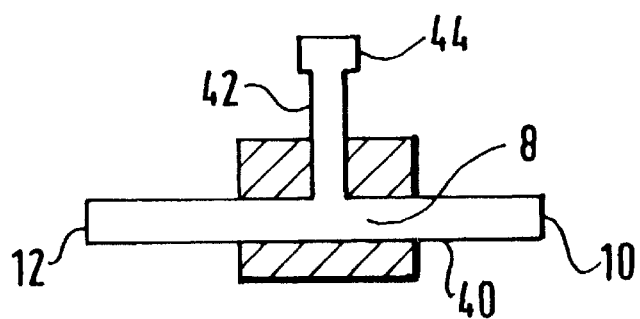
FIG. 3 is a cross-section through a lubricator constituting a second embodiment of the present invention.

The embodiment shown in FIG. 3 is a modification of that shown in FIGS. 1 and 2. A "T" shaped pipe 40 is provided. The through bore of the pipe serves to define a chamber 8 through which the catheter guide wire passes in use. The opposing ends of the pipe define the first and second openings 10 and 12. A side branch 42 acts as a lubricant delivery passage such that lubricant from a syringe attached to a coupling 44 can be introduced into the pipe 40. The pipe 40 is closely dimensioned to the external diameter of the guide wire so as to reduce the rate at which lubricant leaks from the lubricator. However, the pipe is sufficiently larger than the diameter of the guide wire to avoid significant frictional engagement with the guide wire. The lubricant that leaks from the openings 10 and 12 runs along the surface of the guide wire thereby wetting and lubricating it.

Figure 4:
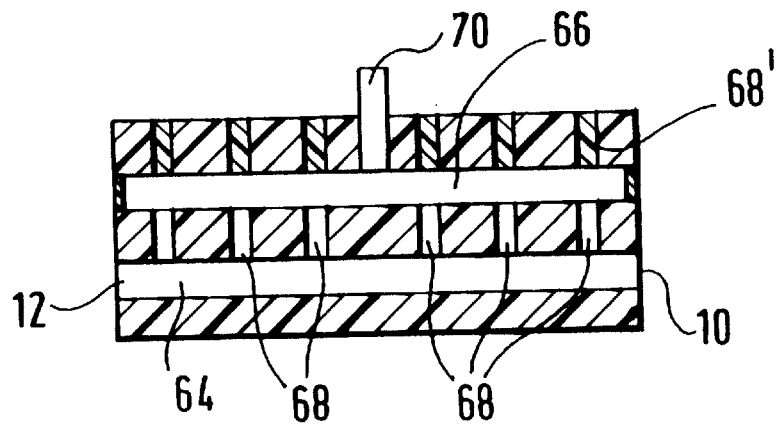
FIG. 4 is a cross-section through a lubricator constituting a third embodiment of the present invention.
Figure 5:
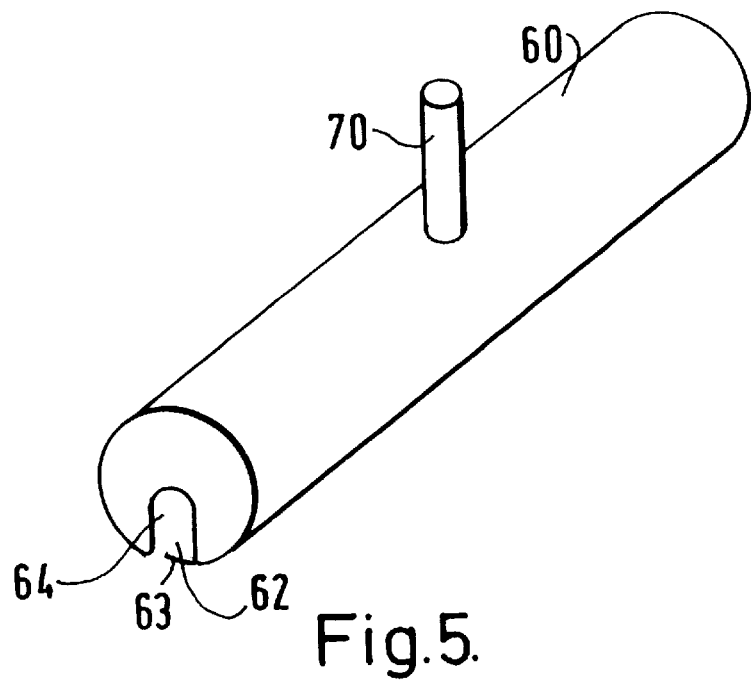
FIG. 5 is a perspective view of the embodiment shown in FIG. 4.

FIGS. 4 and 5 illustrate a further embodiment in which the chamber 8 of the first two embodiments is modified so as to become opened along one edge. The first two embodiments needed the guide wire to be fed through the lubricator. However in this arrangement the lubricator can be pushed laterally onto the guide wire. As shown in FIG. 5, the lubricator body 60 has an opening 62 formed therein. The opening 62 extends along the entire length of the body 60. The opening provides an elongate entry into a channel 64. Optionally a flexible lip 63 may be provided so as to partially or fully close the side of the channel whilst still allowing the catheter guide wire to be moved into the lubricator by pushing it into the opening 62.

In order to distribute fluid evenly within the lubricator a distribution duct 66 (FIG. 4) may be provided adjacent the channel 64. One or more passages 68 link the duct 66 to the channel 64. The duct 66 is in fluid flow communication with a passage 70 through which lubricant can be introduced. The various passages can be formed by drilling through the material of the body and then sealing selected ends of the drillings so as to prevent fluid from escaping from the outer surface of the device. Thus the passages 68' are formed in the creation of massages 68, but are subsequently blanked off.

In use, fluid is introduced from a syringe into passage 70 from where it flows into the channel 64 via the duct 66 and passages 68. The lubricant can then wet the surface of a guide wire in the duct. The lubricator can easily be placed on or removed from a guide wire by passing the wire through the opening 62.

Figure 6:
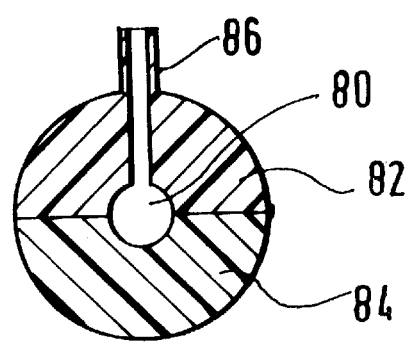
FIG. 6 is a cross-section through a lubricator constituting a further embodiment of the invention.

FIG. 6 shows a cross-section through a lubricator where a channel 80 extends along the lubricator. The channel straddles the junction between two separable halves 82 and 84 of the lubricator body such that the lubricator can be assembled or disassembled around a device, such as a catheter guide wire. As before, lubricant is introduced through a side channel 86.

This construction lends itself to forming the lubricator of porous rigid foam such that the foam can act as a reservoir for the lubricant.

The halves can snap fit together or may be held together by suitable mechanical fastenings (not shown). The halves may be hingedly connected together.

It is thus possible to provide a lubricator and a combination of a lubricator and stabiliser for use with catheter guide wires which eases the passage of the catheter with respect to the guide wire and hence reduces the mechanical force and motion inadvertently transmitted to a patient.

What is claimed is:

1. A lubricator for ex-corporeal lubrication of a catheter guide wire, comprising a channel having first and second openings formed therein, wherein the lubricator can be passed along a guidewire that has been previously inserted with a patient's body, the lubricator further comprising a third opening in liquid communication with the channel arranged to provide a connection to a pressurised liquid source, wherein the first and second openings are dimensioned such that the guide wire can extend therethrough in a non-sealing manner and contact with the contents thereof, and in which the first and second openings are dimensioned so as to be larger than the guide wire such that in use pressurised liquid supplied via the third opening leaks out of both the first and second openings and runs axially along the surface of the guidewire outside of the lubricator, thereby lubricating the guidewire such that the lubricator can be moved substantially freely along the guide wire.

2. A lubricator as claimed in claim 1, in which the first and second openings have a cross-section selected to be slightly greater than the external dimension of the guide wire such that when pressure is removed from the liquid, liquid is retained in the lubricator without substantial leakage through the openings.

3. A lubricator as claimed in claim 1, in which the channel is open along one side thereof such that the guide wire can be introduced into the lubricator via the open side of the channel.

4. A lubricator as claimed in claim 1, comprising a plurality of delivery paths for delivering the liquid to spaced apart regions of the channel.

5. A lubricator as claimed in claim 1, in which the lubricator is provided with an attachment region for releasibly attaching a stabilising device for engaging a medical device.

6. A lubricator as claimed in claim 5, in combination with a guide wire stabiliser, the stabiliser comprising a plurality of engaging elements movable between a first position at which they grip the guide wire so as to inhibit relative motion between the stabiliser and the portion of the guide wire engaged by the stabiliser, and a second position at which the engaging elements move away from the guide wire to a sufficient extent to allow a catheter to be moved along the guide wire and past the engagement elements.

7. A combination of a guide wire lubricator and a stabiliser as claimed in claim 6, in which, in use, the engaging elements of the stabiliser encircle the guide wire.

8. A lubricator as claimed in claim 3, in which the open channel is profiled so as to inhibit its unintentional removal from a guide wire.

9. A lubricator as claimed in claim 3, in which the channel comprises at least one sealing element along the open side thereof.

10. A method of lubricating a catheter guidewire outside a patient's body, the method comprising passing the channel of a lubricator along a guidewire that has been previously inserted within the patients body, the channel having first and second openings therein being dimensioned so as to be larger than the guidewire, connecting a third opening of the lubricator to a supply of pressurised liquid, the third opening being in liquid communication with the channel, such that pressurised liquid leaks through both of the first and second openings and runs axially along the surface of the guidewire outside of the lubricator, and moving the lubricator along the guidewire.

\* \* \* \* \*